(12) United States Patent
Liu et al.

(10) Patent No.: US 11,913,947 B2
(45) Date of Patent: Feb. 27, 2024

(54) DIGITAL IMMUNOCHIP AND MANUFACTURE METHOD OF THE SAME

(71) Applicant: BOE TECHNOLOGY GROUP CO., LTD., Beijing (CN)

(72) Inventors: Haonan Liu, Beijing (CN); Yudan Yin, Beijing (CN); Ding Ding, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 167 days.

(21) Appl. No.: 17/355,338

(22) Filed: Jun. 23, 2021

(65) Prior Publication Data
US 2022/0163516 A1 May 26, 2022

(30) Foreign Application Priority Data
Nov. 26, 2020 (CN) .......................... 202011349414.7

(51) Int. Cl.
| | |
|---|---|
| *G01N 33/68* | (2006.01) |
| *G01N 21/33* | (2006.01) |
| *G01N 21/64* | (2006.01) |
| *G01N 33/52* | (2006.01) |
| *C07C 309/65* | (2006.01) |
| *C07C 309/73* | (2006.01) |
| *A01N 1/02* | (2006.01) |
| *G01N 1/40* | (2006.01) |

(Continued)

(52) U.S. Cl.
CPC .... *G01N 33/5438* (2013.01); *B01L 3/502707* (2013.01); *B01L 3/502715* (2013.01); *B01L 2200/12* (2013.01); *B01L 2300/0819* (2013.01); *B01L 2300/12* (2013.01); *B01L 2300/165* (2013.01)

(58) Field of Classification Search
CPC .......... G01N 33/5438; G01N 33/54306; B01L 3/502707; B01L 3/502715; B01L 2200/12; B01L 2300/0819; B01L 2300/12; B01L 2300/165; B01L 3/502792; B01L 2200/16; B01L 2300/161
See application file for complete search history.

(56) References Cited

U.S. PATENT DOCUMENTS

2022/0362779 A1\* 11/2022 Jagtiani .............. G01N 15/0656

FOREIGN PATENT DOCUMENTS

| CN | 114686374 A | \* | 7/2022 | |
| WO | WO-2018210104 A1 | \* | 11/2018 | ............ B01L 3/5027 |

\* cited by examiner

*Primary Examiner* — Jennifer Wecker
*Assistant Examiner* — Oyeleye Alexander Alabi
(74) *Attorney, Agent, or Firm* — HOUTTEMAN LAW LLC (57) ABSTRACT

The present disclosure provides a digital immunochip and a manufacture method thereof. The digital immunochip includes a first substrate and a second substrate which are opposite to each other. The first substrate includes: a first base substrate; at least one driving electrode on the first base substrate and configured to drive an object to be detected to move; a dielectric layer on a side of the at least one driving electrode away from the first base substrate and covering the at least one driving electrode; and a first hydrophobic layer on a side of the dielectric layer away from the first base substrate. The second substrate includes: a second base substrate; and an immunoassay substance on a side of the second base substrate proximal to the first hydrophobic layer of the first substrate and including an antigen or an antibody.

12 Claims, 3 Drawing Sheets

(51) Int. Cl.
*G01N 33/543* (2006.01)
*B01L 3/00* (2006.01)

DIGITAL IMMUNOCHIP AND MANUFACTURE METHOD OF THE SAME

CROSS-REFERENCE TO RELATED APPLICATIONS

The present disclosure claims the priority to Chinese Patent Application No. 202011349414.7, filed on Nov. 26, 2020, the contents of which are incorporated herein by reference in its entirety.

TECHNICAL FIELD

The present disclosure relates to the field of immunoassay chips, and in particular, to a digital immunochip and a manufacture method of the same.

BACKGROUND

Immunoassay is a method for determining an antigen or an antibody in a sample through a specific reaction between the antigen and the antibody, and has the advantages such as a high selectivity, a high sensitivity, a wide application range and the like. After years of application and development, immunoassay has become a powerful means in clinical diagnosis, biomedicine and environmental chemical research. The immunoassay is also applicable to the detection of a trace analyte in a body fluid sample based on specific binding of the antigen and the antibody.

SUMMARY

As an aspect, a digital immunochip is provided. The digital immunochip includes a first substrate and a second substrate opposite to each other. The first substrate includes: a first base substrate; at least one driving electrode on the first base substrate and configured to drive an object to be detected to move; a dielectric layer on a side of the at least one driving electrode away from the first base substrate and covering the at least one driving electrode; and a first hydrophobic layer on a side of the dielectric layer away from the first base substrate. The second substrate includes: a second base substrate; and an immunoassay substance on a side of the second base substrate proximal to the first hydrophobic layer of the first substrate and including an antigen or an antibody.

In an embodiment, the second substrate further includes a second hydrophobic layer between the immunoassay substance and the second base substrate, and at least one sample portion in the second hydrophobic layer or on a side of the second hydrophobic layer proximal to the first substrate and configured to carry the immunoassay substance thereon.

In an embodiment, the at least one sample portion is in a groove of the second hydrophobic layer, and a surface of the second hydrophobic layer proximal to the first substrate and is on the same plane as a surface of the at least one sample portion proximal to the first substrate.

In an embodiment, the at least one sample portion has a thickness the same as a thickness of the second hydrophobic layer.

In an embodiment, the at least one driving electrode includes a plurality of driving electrodes arranged in a plurality of rows and a plurality of columns, the at least one sample portion includes a plurality of sample portions arranged in a plurality of rows and a plurality of columns, the plurality of sample portions are in one-to-one correspondence with the plurality of driving electrodes, and an entire orthographic projection of each of the plurality of sample portions on the first base substrate is within an orthographic projection of a driving electrode corresponding to the sample portion on the first base substrate.

In an embodiment, the digital immunochip has a plurality of sample regions, the immunoassay substance in a sample region of the plurality of sample regions is different from the immunoassay substance in another sample region of the plurality of sample regions, and each of the plurality of sample regions is provided with a portion of the plurality of driving electrodes and the immunoassay substance therein.

In an embodiment, the at least one sample portion includes silicon dioxide.

In an embodiment, the first hydrophobic layer includes: at least one of teflon and silicon nitride.

In an embodiment, the second hydrophobic layer includes at least one of teflon and silicon nitride.

In an embodiment, the first base substrate is a glass substrate, the second base substrate is a glass substrate, the at least one driving electrode includes a conductive metal, and the dielectric layer includes aluminum oxide or tantalum pentoxide.

In an embodiment, the digital immunochip further includes an inlet, through which the substance to be detected enters the digital immunochip; an outlet, through which the substance to be detected exits the digital immunochip, and a driving circuit, configured to provide a driving signal to the at least one driving electrode.

As an aspect, a digital immunochip is provided. The digital immunochip includes: a first substrate including a first base substrate; at least one driving electrode on the first base substrate and configured to drive an object to be detected to move; a dielectric layer on a side of the at least one driving electrode away from the first base substrate and covering the at least one driving electrode, and a first hydrophobic layer on a side of the dielectric layer away from the first base substrate; and a second substrate including a second base substrate; an immunoassay substance on a side of the second base substrate proximal to the first hydrophobic layer of the first substrate and including an antigen or an antibody; a second hydrophobic layer between the immunoassay substance and the second base substrate; and at least one sample portion in the second hydrophobic layer and configured to carry the immunoassay substance thereon. The at least one sample portion has a thickness the same as a thickness of the second hydrophobic layer. The at least one driving electrode includes a plurality of driving electrodes, the at least one sample portion includes a plurality of sample portions, the plurality of sample portions are in one-to-one correspondence with the plurality of driving electrodes, and an entire orthographic projection of each of the plurality of sample portions on the first base substrate is within an orthographic projection of a driving electrode corresponding to the sample portion on the first base substrate.

As yet another aspect, a method for manufacturing a digital immunochip is provided. The method includes: sequentially forming a driving electrode, a dielectric layer and a first hydrophobic layer on a first base substrate to form a first substrate; forming a plurality of sample portions on a second base substrate through a patterning process; forming an immunoassay substance on the plurality of sample portions to form a second substrate; and aligning and assembling the first substrate and the second substrate to form the digital immunochip.

In an embodiment, the forming the plurality of sample portions on the second base substrate through the patterning process includes: forming a second hydrophobic film layer and a photoresist layer on the second base substrate; removing a portion of the photoresist layer and the corresponding second hydrophobic film layer through an etching process to form a patterned photoresist layer and a patterned second hydrophobic layer; forming a sample portion film layer on the second base substrate, such that a portion of the sample portion film layer falls into hollow-out regions of the second hydrophobic layer, and the other portion of the sample portion film layer is on a side of the photoresist layer away from the second base substrate; and removing, through a stripping process, the patterned photoresist layer and the other portion of the sample portion film layer on the side of the photoresist layer away from the second base substrate, so as to form the plurality of sample portions.

In an embodiment, the forming the immunoassay substance on the plurality of sample portions includes: performing a hydroxyl-group activation on a surface of the plurality of sample portions to obtain the activated surface containing a hydroxyl group; modifying the hydroxyl group with an amino group, after the hydroxyl-group activation is finished; modifying the amino group with a carboxyl group after the amino group is modified; and modifying the plurality of sample portions with the immunoassay substance by bonding the immunoassay substance and the carboxyl group, after the carboxyl group is modified.

In an embodiment, the aligning and assembling the first substrate and the second substrate to form the digital immunochip includes bonding the first substrate and the second substrate through a frame sealing adhesive.

DETAILED DESCRIPTION

In order to make those skilled in the art better understand the technical solutions of the present disclosure, the present disclosure is further described in detail below with reference to the accompanying drawings and specific embodiments.

In an embodiment of the present disclosure, a patterning process, such as a photolithographic patterning process, includes: coating a photoresist layer on a structural layer to be patterned through a spin-coating, blade-coating or roller-coating process; exposing the photoresist layer by using a mask plate; performing a development process on the exposed photoresist layer to obtain a photoresist pattern; etching the structural layer by using the photoresist pattern, and optionally, removing the photoresist pattern; and finally stripping off the remaining photoresist pattern to form the desired structure.

In the embodiment of the present disclosure, the patterning process may include multiple exposure, development or etching processes according to various patterns, and the specific pattern formed on the same layer may be a continuous or discontinuous pattern, and may be at different heights or have different thicknesses.

As shown in FIGS. 1 to 5, the embodiment provides a digital immunochip for detecting a reagent (i.e., a substance to be detected) containing an immune substance. The digital immunochip provided by the embodiment includes: a first substrate and a second substrate that are disposed opposite (i.e., counter) to each other. The first substrate includes: a first base substrate 11, at least one driving electrode 12 disposed on the first base substrate 11; a first hydrophobic layer 13 arranged on a side of a layer, on which the driving electrode 12 is located, away from the first base substrate 11; and a dielectric layer 14 disposed between the driving electrode 12 and the first hydrophobic layer 13. The second substrate includes: a second base substrate 21, an immunoassay substance 22 disposed on the second base substrate 21. The immunoassay substance 22 is arranged on a side of the second substrate proximal to the first substrate and includes an antigen or an antibody.

In the digital immunochip of the embodiment, the immunoassay is combined with the digital microfluidic chip, and the immunoassay substance 22 is disposed on the second substrate of the digital immunochip. The digital immunochip can transmit reagent containing the immune substance and a cleaning solution based on a dielectric wetting technology. The reagent droplet is driven to move by controlling an electrical signal of the driving electrode 12, so that the reagent droplet can move over the digital immunochip. The immune substance in the reagent droplet may be automatically bonded with the immunoassay substance 22 on the second substrate. After the digital immunochip is cleaned by using the cleaning solution, the reagent containing a fluorescent direct-labeled immunoassay substance 22 is transmitted over the digital immunochip again, and then the fluorescent direct-labeled immunoassay substance 22 is recognized and bonded with the bonded immune substance again. After that, the digital immunochip is cleaned again and then placed under a fluorescence microscope for fluorescence detection, so that the immune complex may be detected, and the detection of the immune substance (e.g., an antigen) is realized.

In existing art, the immunoassay method is to fix an immunoassay substance 22 (i.e., an antibody or an antigen) on a surface of a well plate, add a sample to be detected and incubate for about two hours; separate an immune complex from the mixture after the reaction is completed; and determine an amount of the substance to be detected contained in the sample to be detected by determining an amount of the immune complex. However, the method has the defects such as a complex operation, more reagent consumption, a low flux, a larger difference in analysis result for various operators and the like. The digital immunochip based on the embodiment can modify the antibody on the glass substrate, and accurately control the sample to be detected to move and accurately react therein by using the dielectric wetting principle, realize the detection of immune substances in the reagent by using only a small amount of reagent droplet, and has the advantages such as a high flux, a low reagent consumption, a rapid reaction, a few artificial influence factors and the like.

The digital immunochip provided by the embodiment is realized based on the binding property of an antigen and an antibody when the digital immunochip is used for immunoassay. In the embodiment, the immunoassay substance 22 disposed on the second substrate is different according to different immune substances to be detected. For example, when an antigen in the reagent is to be detected, the immunoassay substance 22 on the second base substrate 21 is an antibody, and the antigen and the antibody are corresponding immune substances. When an antigen in the reagent is to be detected, the immunoassay substance 22 on the second base substrate 21 is an antibody. When an antibody in the reagent is to be detected, the immunoassay substance 22 on the second base substrate 21 is an antigen. In the following embodiment, an example in which an antigen in the reagent is to be detected by using the immunoassay substance 22, which is a corresponding antibody, on the second base substrate 21 is illustrated.

The digital immunochip of the embodiment can drive, in a single-board driving way, the reagent to flow. As shown in FIGS. 1 to 5, in the digital immunochip of the embodiment, at least one driving electrode is disposed on the first substrate, and in an example, a plurality of driving electrodes 12 are disposed on the first substrate. Specifically, the first substrate includes a first base substrate 11, and a plurality of driving electrodes 12 arranged on a surface (i.e., an upper surface in FIG. 2) of the first base substrate 11 in a bonding manner.

The immunoassay process of the digital immunochip according to the embodiment includes:

(1) Supplying a reagent droplet onto the digital immunochip; and driving by the driving electrode 12, the reagent droplet to move to a desired position, such that the antigen in the reagent droplet is fully recognized by and bonded with the antibody on the second substrate in the sample region;

(2) Supplying a cleaning solution into the digital immunochip; and cleaning the digital immunochip by controlling droplets of the cleaning solution to move therethrough;

(3) Supplying a reagent containing a fluorescent direct-labeled antibody into the digital immunochip; and driving, by the driving electrode 12, the reagent to move to a sample region, so that the fluorescent direct-labeled antibody is bonded with the bonded antigen and antibody, that is, a double-antibody sandwich.

(4) Supplying the cleaning solution into the digital immunochip again; and cleaning the digital immunochip by controlling the droplets of the cleaning solution to move therethrough; and (5) Placing the digital immunochip under a fluorescence microscope for fluorescence detection and quantitative analysis.

In the digital immunochip provided by the embodiment, only a small amount of reagent droplet is required to detect the component and concentration of the immune substance in the reagent droplet. In the embodiment, a sufficient amount of immunoassay substance is modified in the digital immunochip. By sufficiently binding the reagent droplet and the immunoassay substance, the antigen corresponding to the antibody and in the reagent droplet may be detected, and a component of the immune substance in the actual reagent droplet may be detected. It is understood that, in the embodiment, only a small amount of reagent droplet is required to detect the component of the immune substance in the reagent droplet in the case of a sufficient amount of antibody.

In practice, the reagent often contains multiple types of immune substances (e.g., multiple different types of antigens). Optionally, in an embodiment, the digital immunochip includes a plurality of sample regions, and a portion of the plurality of driving electrodes 12 (e.g., one or more driving electrodes) and the immunoassay substance 22 are disposed in each of the plurality of sample regions. The immunoassay substances 22 in at least a portion of the plurality of sample regions are different from each other. Since the immunoassay substances 22 in at least a portion of the plurality of sample regions are different from each other, the multiple antigens in the reagent droplet can be detected at a time. Specifically, when the reagent droplet is detected, the droplet may be controlled to reach a first sample region, so that the antibody (assumed as a first antibody) in the first sample region is fully bonded with the antigen (i.e., a first antigen corresponding to the first antibody) in the reagent droplet. After the bonding is completed, the reagent droplet is driven to a second sample region by controlling the driving electrode 12, so that the antibody (assumed as a second antibody) in the second sample region is bonded with the antigen (i.e., a second antigen corresponding to the second antibody) in the reagent droplet, . . . , and so on. The reagent droplet may be respectively bonded and reacted with different antibodies in various sample regions. And then, the digital immunochip is cleaned by using the cleaning solution; and then, the liquid droplets of a test solution containing the fluorescent-labeled antibody flow to the sample regions, are recognized by and bonded with the corresponding antigens adsorbed in the sample regions, so that different antigens can be detected all at once.

The liquid droplets of the test solution containing the fluorescent-labeled antibody, which are one liquid drop mixed with a plurality of antibodies on which a fluorescent label is labeled, or alternatively are liquid drops containing different fluorescent-labeled antibodies, are respectively transmitted to a sample region for reaction. This is not limited in the embodiment.

Figure 1:
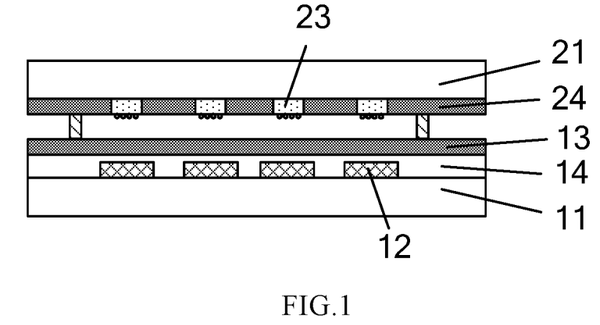
FIG. 1 is a schematic diagram showing a structure of a digital immunochip according to an embodiment of the present disclosure.
Figure 2:
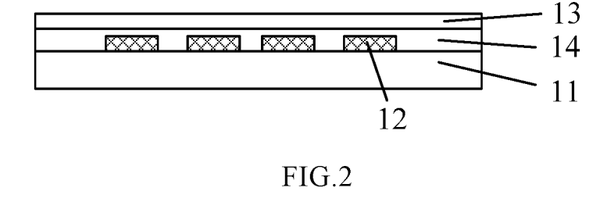
FIG. 2 is a schematic diagram showing a structure of a first substrate of a digital immunochip according to an embodiment of the present disclosure.

In the embodiment, as shown in FIG. 2, a material of the first base substrate 11 may include glass. A material of the driving electrode 12 may include a conductive metal. A size of the driving electrode 12 may be determined according to a size of the droplet to be controlled and a size of the sample portion 23. The first hydrophobic layer 13, on which the reagent droplet has a larger initial contact angle, is disposed above a layer on which the driving electrodes 12 are located (i.e., on a side of the layer away from the first base substrate 11), so as to reduce adhesion of the sample to the electrodes, reduce the movement resistance of the droplet, and reduce the possibility of cross contamination between samples. A material of the first hydrophobic layer 13 may include at least one of teflon, silicon nitride, etc. A dielectric layer 14 is also formed between the layer of the driving electrodes 12 and the first hydrophobic layer 13 to prevent breakdown of the driving electrodes 12. Specifically, a material of the dielectric layer 14 may include aluminum oxide, tantalum pentoxide ($Ta_2O_5$), and the like.

Figure 3:
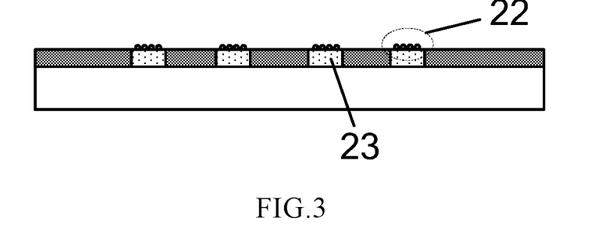
FIG. 3 is a schematic diagram showing a structure of a second substrate of a digital immunochip according to an embodiment of the present disclosure.
Figure 4:
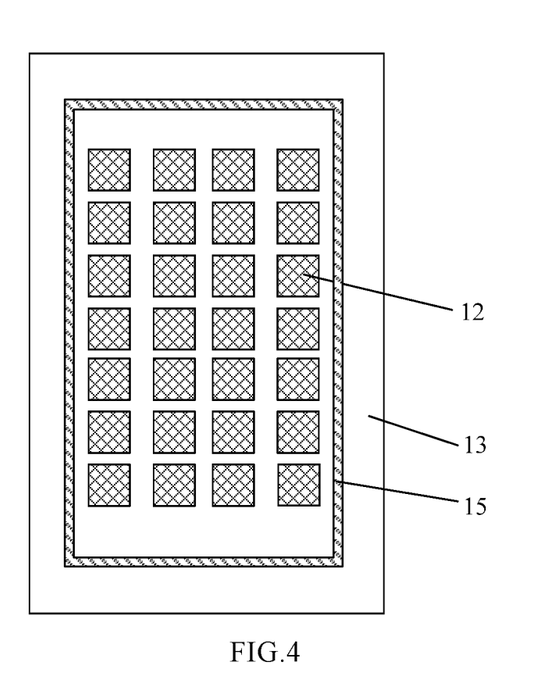
FIG. 4 is a schematic diagram showing a structure of a first substrate of a digital immunochip according to an embodiment of the present disclosure.
Figure 5:
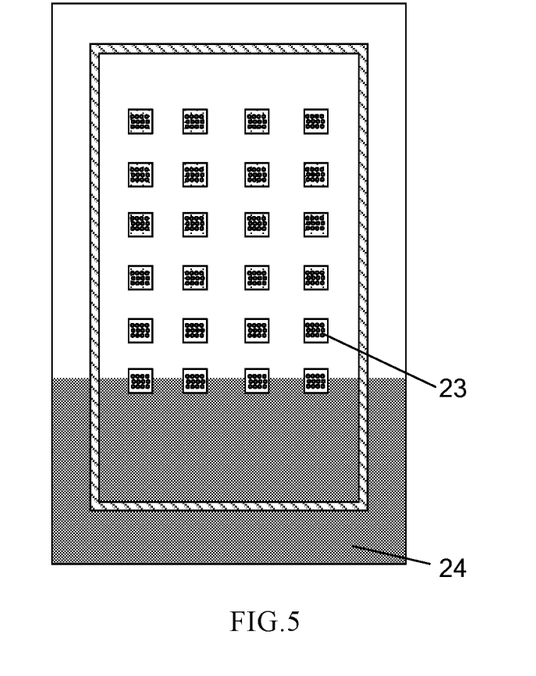
FIG. 5 is a schematic diagram showing a structure of a second substrate of a digital immunochip according to an embodiment of the present disclosure.

Optionally, as shown in FIGS. 3 and 5, in each of the sampling regions, the second substrate further includes: a sample portion 23, and the immunoassay substance 22 is provided on a side of the sample portion 23 proximal to the first substrate. That is, the arrangement of the immunoassay substance 22 on the second substrate is realized through the arrangement of the immunoassay substance 22 on the sample portion 23. It is to be understood that the second base substrate 21 is generally made of glass or the like, similar to the first base substrate 11. In the embodiment, the formation of the antibody on the second base substrate 21 is achieved by modifying the antibody on the sample portion 23.

A material of the sample portion 23 may include silicon dioxide.

Further optionally, the second substrate further includes: a second hydrophobic layer 24 on the same layer as the sample portion 23 or on a side of the sample portion 23 proximal to the first substrate. In the embodiment, since the reagent droplet on the second hydrophobic layer 24 has a larger initial contact angle, the adhesion and residue of the sample on the second substrate can be decreased, the movement resistance of the droplet can be decreased, and the possibility of cross contamination between samples can be reduced. Specifically, a material of the second hydrophobic layer 24 may include at least one of teflon, silicon nitride, or the like.

Further optionally, the sample portion 23 is located in a via hole of the second hydrophobic layer 24. A surface of the second hydrophobic layer 24 proximal to the first substrate is on the same plane as a surface of the sample portion 23 proximal to the first substrate. That is to say, the surface of the second substrate proximal to the first substrate (i.e., a lower surface of the second substrate) is a plane, so that the lower surface of the second substrate can be kept smooth and hydrophobic as much as possible, thereby reducing the adhesion and residue of the sample on the second substrate, and reducing the movement resistance of the droplet.

Optionally, as shown in FIG. 3, the second hydrophobic layer 24 is disposed in the same layer and has the same thickness as the sample portion 23. Arrangement in the same layer refers to arrangement in the same layer in visual perception, that is, a distance from the second hydrophobic layer 24 to the second base substrate 21 is the same as a distance from the sample portion 23 to the second base substrate 21. Specifically, in the embodiment, the second hydrophobic layer 24 may be a patterned film structure, and the sample portion 23 may be located in a hollow region of the second hydrophobic layer 24. In an embodiment, the second hydrophobic layer 24 has a plurality of vias exposing the surface of the second base substrate, and silicon dioxide is filled in the plurality of via holes to form the sample portions 23. On this basis, since a thickness of the sample portion 23 is the same as that of the second hydrophobic layer 24, the surface of the sample portion 23 proximal to the first substrate together with the surface of the second hydrophobic layer 24 proximal to the first substrate form a plat surface.

It should be understood that, in the embodiment, the sample portion 23 may be disposed on a side of the second hydrophobic layer 24 proximal to the first substrate, instead of being disposed on the same layer as the second hydrophobic layer 24. Specifically, the sample portion 23 may be arranged directly on a side of the second hydrophobic layer 24 proximal to the first substrate. In an embodiment, a groove is formed in the second hydrophobic layer 24, and the sample portion 23 is disposed in the groove, so that a surface of the second hydrophobic layer 24 proximal to the first substrate and a surface of the sample portion 23 proximal to the first substrate are located on the same plane.

Optionally, the sample portions 23 are in one-to-one correspondence with the driving electrodes 12. An orthographic projection of the sample portion 23 on the first base substrate 11 is smaller than an orthographic projection of the corresponding driving electrode 12 on the first base substrate 11. An entire orthographic projection of each of the sample portions 23 on the first base substrate 11 is within an orthographic projection of a driving electrode 12 corresponding to the sample portion on the first base substrate 11. In the embodiment, the driving electrodes 12 drive the reagent droplet to the respective sample regions, and the reagent droplet reacts with the antibody on the sample portion 23. Since an area of the driving electrode 12 is larger than that of the sample portion 23, the contact surface between the reagent droplet and the sample portion 23 can be ensured as much as possible, so that the antigen and the antibody can be fully bonded, and the detection precision can be improved.

It can be understood that the digital immunochip in the embodiment is further provided with a reagent inlet, a reagent outlet, a driving circuit, and other structures, and the specific arrangement of the digital immunochip can refer to relevant content of the digital microfluidic chip, and will not be described in detail herein.

In an embodiment, a method for manufacturing any one of above digital immunochips is provided. The method includes steps S1 to S4.

At step S1, a driving electrode 12 and a first hydrophobic layer 13 are sequentially formed on a first base substrate 11 to form a first substrate.

Specifically, step S1 includes: forming a conductive layer on the first base substrate 11; removing a portion of the conductive layer through an etching process to form a plurality of driving electrodes 12; forming a dielectric layer 14 on the driving electrodes 12 through a film forming process; and forming a first hydrophobic layer 13 on the dielectric layer 14 through processes such as spin coating and drying process.

At step S2, a plurality of sample portions 23 are formed on the second base substrate 21 through a patterning process.

Step S2 specifically includes: forming a sample portion film layer 23A on the second base substrate 21; removing a portion of the sample portion film layer 23A through an etching process to form one or more sample portions 23.

Figure 6:
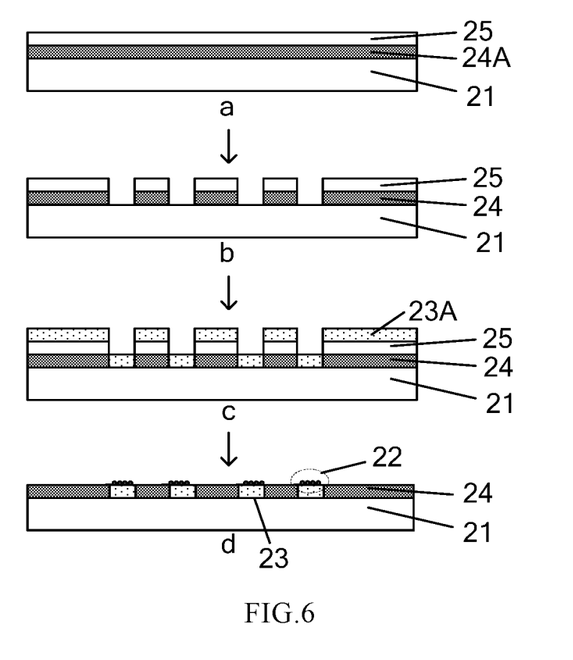
FIG. 6 is a flow chart showing a method for manufacturing a second substrate of a digital immunochip according to an embodiment of the present disclosure.

Preferably, the embodiment further includes: a step of forming a second hydrophobic layer 24 on the base substrate. In this case, as shown in FIG. 6, the forming of the plurality of sample portions 23 includes: forming a second hydrophobic film layer 24A and a photoresist layer 25 on the base substrate; removing a portion of the photoresist layer 25 and the corresponding second hydrophobic film layer 24A through an etching process to form a patterned photoresist layer 25 and a patterned second hydrophobic layer 24; forming a sample portion film layer 23A on the second base substrate 21, such that a portion of the sample portion film layer 23A falls into the hollow-out regions of the second hydrophobic layer 24, and the other portion of the sample portion film layer 23A is located on a side of the photoresist layer 25 away from the second base substrate 21; removing, through a stripping process, the patterned photoresist layer 25 along with the other portion of the sample portion film layer 23A on the side of the photoresist layer 25 away from the second base substrate 21, so as to form the plurality of sample portions 23.

At step S3, the immunoassay substance 22 is modified and formed on the sample portion 23, so as to form a second substrate.

Specifically, step S3 may include: performing a hydroxyl-group activation on a surface of the plurality of sample portions to obtain the activated surface containing a hydroxyl group; modifying the hydroxyl group with an amino group;

modifying the amino group with a carboxyl group; and modifying the plurality of sample portions with a required antibody by bonding the required antibody and the carboxyl group.

At step S4, the first substrate and the second substrate are aligned and assembled together.

In this step, the first substrate and the second substrate are bonded by the frame sealing adhesive 15 and the like. The first substrate has a surface, on which the driving electrode 12 is formed, facing the second substrate, and the second substrate has a surface, on which the immunoassay substance 22 is located, facing the first substrate.

It should be understood that the above implementations are merely exemplary embodiments for the purpose of illustrating the principles of the present disclosure, however, the present disclosure is not limited thereto. It will be apparent to those skilled in the art that various changes and modifications can be made without departing from the spirit and essence of the present disclosure, which are also to be regarded as the scope of the present disclosure.

What is claimed is:

1. A digital immunochip, comprising a first substrate and a second substrate opposite to each other; wherein
the first substrate comprises:
a first base substrate;
at least one driving electrode on the first base substrate and configured to drive an object to be detected to move;
a dielectric layer on a side of the at least one driving electrode away from the first base substrate and covering the at least one driving electrode, and
a first hydrophobic layer on a side of the dielectric layer away from the first base substrate; and
the second substrate comprises:
a second base substrate; and
an immunoassay substance on a side of the second base substrate proximal to the first hydrophobic layer of the first substrate and comprising an antigen or an antibody
the second substrate further comprises:
a second hydrophobic layer between the immunoassay substance and the second base substrate and having a plurality of via holes exposing a lower surface of the second base substrate, and
a plurality of sample portions filled in plurality of via holes formed in the second hydrophobic layer and configured to carry the immunoassay substance thereon, wherein
a surface of the second hydrophobic layer proximal to the first substrate is a flat surface, surfaces of the plurality of sample portions proximal to the first substrate are flat surfaces, and the surface of the second hydrophobic layer proximal to the first substrate is on the same plane as the surfaces of the plurality of sample portions proximal to the first substrate, and
the plurality of sample portions have a thickness the same as a thickness of the second hydrophobic layer.

2. The digital immunochip of claim 1, wherein
the at least one driving electrode comprises a plurality of driving electrodes arranged in a plurality of rows and a plurality of columns,
the plurality of sample portions are arranged in a plurality of rows and a plurality of columns,
the plurality of sample portions are in one-to-one correspondence with the plurality of driving electrodes, and
an entire orthographic projection of each of the plurality of sample portions on the first base substrate is within an orthographic projection of a driving electrode corresponding to the sample portion on the first base substrate.

3. The digital immunochip of claim 1, wherein
the digital immunochip has a plurality of sample regions,
the immunoassay substance in a sample region of the plurality of sample regions is different from the immunoassay substance in another sample region of the plurality of sample regions, and
each of the plurality of sample regions is provided with a portion of the plurality of driving electrodes and the immunoassay substance therein.

4. The digital immunochip of claim 1, wherein the plurality of sample portions comprises silicon dioxide.

5. The digital immunochip of claim 1, wherein the first hydrophobic layer comprises at least one of teflon or silicon nitride.

6. The digital immunochip of claim 1, wherein the second hydrophobic layer comprises at least one of teflon or silicon nitride.

7. The digital immunochip of claim 1, wherein
the first base substrate is a glass substrate,
the second base substrate is a glass substrate,
the at least one driving electrode comprises a conductive metal, and
the dielectric layer comprises aluminum oxide or tantalum pentoxide.

8. The digital immunochip of claim 1, further comprising:
an inlet, through which the object to be detected enters the digital immunochip;
an outlet, through which the object to be detected exits the digital immunochip; and
a driving circuit, configured to provide a driving signal to the at least one driving electrode.

9. A digital immunochip, comprising:
a first substrate comprising:
a first base substrate;
at least one driving electrode on the first base substrate and configured to drive an object to be detected to move;
a dielectric layer on a side of the at least one driving electrode away from the first base substrate and covering the at least one driving electrode, and
a first hydrophobic layer on a side of the dielectric layer away from the first base substrate; and
a second substrate comprising:
a second base substrate;
an immunoassay substance on a side of the second base substrate proximal to the first hydrophobic layer of the first substrate and comprising an antigen or an antibody;
a second hydrophobic layer between the immunoassay substance and the second base substrate and having a plurality of via holes exposing a lower surface of the second base substrate; and
a plurality of sample portions filled in plurality of via holes formed in the second hydrophobic layer and configured to carry the immunoassay substance thereon, wherein
a surface of the second hydrophobic layer proximal to the first substrate is a flat surface, surfaces of the plurality of sample portions proximal to the first substrate are flat surfaces, and the surface of the second hydrophobic layer proximal to the first substrate is on the same plane as the surfaces of the plurality of sample portions proximal to the first substrate, the plurality of sample portions have a thickness the same as a thickness of the second hydrophobic layer, the at least one driving electrode comprises a plurality of driving electrodes, the plurality of sample portions are in one-to-one correspondence with the plurality of driving electrodes, and an entire orthographic projection of each of the plurality of sample portions on the first base substrate is within an orthographic projection of a driving electrode corresponding to the sample portion on the first base substrate.

10. A method for manufacturing a digital immunochip, comprising:

sequentially forming a driving electrode, a dielectric layer and a first hydrophobic layer on a first base substrate to form a first substrate;

forming a plurality of sample portions on a second base substrate through a patterning process;

forming an immunoassay substance on the plurality of sample portions to form a second substrate; and aligning and assembling the first substrate and the second substrate to form the digital immunochip, wherein forming the plurality of sample portions on the second base substrate through the patterning process comprises:

forming a second hydrophobic film layer and a photoresist layer on the second base substate;

removing a portion of the photoresist layer and the corresponding second hydrophobic film layer through an etching process to form a patterned photoresist layer and a patterned second hydrophobic layer;

forming a sample portion film layer on the second base substrate, such that a portion of the sample portion film layer falls into a plurality of via holes exposing a lower surface of the second base substrate, and the other portion of the sample portion film layer is on a side of the photoresist layer away from the second base substrate; and removing, through a stripping process, the patterned photoresist layer and the other portion of the sample portion film layer on the side of the photoresist layer away from the second base substrate, so as to form the plurality of sample portions, wherein a surface of the patterned second hydrophobic layer proximal to the first substrate is a flat surface, surfaces of the plurality of sample portions proximal to the first substrate are flat surfaces, and the surface of the patterned second hydrophobic layer proximal to the first substrate is on the same plane as the surfaces of the plurality of sample portions proximal to the first substrate, and the plurality of sample portions have a thickness the same as a thickness of the patterned second hydrophobic layer.

11. The method of claim 10, wherein the forming the immunoassay substance on the plurality of sample portions comprises:

performing a hydroxyl-group activation on a surface of the plurality of sample portions to obtain the activated surface containing a hydroxyl group;

modifying the hydroxyl group with an amino group, after the hydroxyl-group activation is finished;

modifying the amino group with a carboxyl group after the amino group is modified; and modifying the plurality of sample portions with the immunoassay substance by bonding the immunoassay substance and the carboxyl group, after the carboxyl group is modified.

12. The method of claim 10, wherein the aligning and assembling the first substrate and the second substrate to form the digital immunochip comprises:

bonding the first substrate and the second substrate through a frame sealing adhesive.

* * * * *